United States Patent
Connor

(10) Patent No.: US 8,850,614 B1
(45) Date of Patent: *Oct. 7, 2014

(54) GARMENT LINER

(76) Inventor: Trudy Connor, Tucson, AZ (US)

( * ) Notice: Subject to any disclaimer, the term of this patent is extended or adjusted under 35 U.S.C. 154(b) by 274 days.

This patent is subject to a terminal disclaimer.

(21) Appl. No.: 13/243,689

(22) Filed: Sep. 23, 2011

Related U.S. Application Data

(63) Continuation of application No. 11/285,883, filed on Nov. 23, 2005, now Pat. No. 8,042,194, which is a continuation-in-part of application No. 10/267,325, filed on Oct. 8, 2002, now abandoned.

(51) Int. Cl.
*A41D 27/12* (2006.01)
*A61F 13/472* (2006.01)

(52) U.S. Cl.
USPC .............................................. 2/46; 604/387

(58) Field of Classification Search
USPC ................................ 604/359, 377
See application file for complete search history.

(56) References Cited

U.S. PATENT DOCUMENTS

| | | | | |
|---|---|---|---|---|
| 4,244,367 A | * | 1/1981 | Rollenhagen | 604/396 |
| 6,591,425 B1 | * | 7/2003 | Zellers | 2/54 |
| 7,048,706 B2 | * | 5/2006 | Cea | 602/26 |
| 2001/0018578 A1 | * | 8/2001 | Imai et al. | 604/364 |
| 2004/0015145 A1 | * | 1/2004 | Miura et al. | 604/367 |

* cited by examiner

*Primary Examiner* — Susan Su
(74) *Attorney, Agent, or Firm* — Rodney J. Fuller; Booth Udall Fuller, PLC

(57) ABSTRACT

Special articles are fashioned as undergarments of a very brief nature, preferably a panty substitute. Brevity, with regard to undergarments has advantages including: comfort and ease of use, improved cooperation with outerwear and protection against soiling. The articles of the invention provide underwear function and feel. The articles are configured to be an underwear substitute without bunching, chafing, or forming visible panty lines. The underwear substitute provides comfort to the user similar to underwear without forming visible panty lines while protecting the outer garment against soiling.

12 Claims, 9 Drawing Sheets

GARMENT LINER

RELATED APPLICATION DATA

This application is a continuation of U.S. patent application Ser. No. 11/285,883, filed Nov. 23, 2005, now U.S. Pat. No. 8,042,194, which is a continuation-in-part of U.S. patent application Ser. No. 10/267,325 filed Oct. 8, 2002, now abandoned.

BACKGROUND OF THE INVENTION

1. Field

The following invention disclosure is generally concerned with articles of clothing and articles used in conjunction with clothing and specifically concerned with liner articles which may be used instead of underwear.

2. Prior Art

It is essential for good hygiene that one wear underwear beneath one's outer clothing. Not only does underwear protect outer clothing from being soiled from the inside, it also protects a wearer from chaffing from the outer clothing. However, underwear is sometimes an inconvenience. It tends to annoy wearers as it is restrictive, tends to bunch and bind, may cause one to become hot, and is accompanied by other adverse side effects. Ladies clothing which is sometimes form fitting particularly presents issues with underwear use. More specifically, underwear may cause panty lines which become visible through outer clothing. Recently, 'thong' type underwear has become quite popular as it reduces panty lines and allows a more perfect and pleasing fit. However, thong type underwear may be uncomfortable to wear.

Wearing no underwear at all is undesirable for the reason that it leaves outer garments exposed to undesirable soiling and further leaves sensitive flesh exposed to the discomfort of contact with rough materials from which outer garments may be made.

The art is replete with panty liners and devices arranged to couple with and protect panties during menstruation. These arrangements invariably include devices operable for absorbing and containing appreciable amounts of fluid and associated matter. As such, they are generally thick and bulky and therefore not suitably worn in conjunction with certain outer garments such as tight fitting pants.

Similarly, products are now offered to persons afflicted with bladder control difficulties, for example, DEPENDS. These devices also are arranged as highly absorbent protective articles. Consequently, they are quite thick and bulky and they consume a significant volume which cannot be hidden in tight fitting clothes, i.e., they must be worn with loose fitting outer garments.

As for lining fashioned to cooperate with the outer garment, one will recall that a bathing suit typically has a sewn-in liner. This liner is well suited to protect the bathing suit from soiling while also providing comfort to the wearer. However, these liners are permanently affixed to the suit and they are not disposable. They typically have reinforced peripheries which tend to be bulky and cause creases and visible lines.

Other pant liner systems include those which are used in conjunction with a fireman's outerwear. U.S. Pat. No. 5,095,549 is representative. An outerwear pant requires a liner for the comfort and cleanliness of the wearer. The liner is disposed next to the interior surface of the pants and affixed thereto. As such, it shares important concepts presented here following and is considered prior art.

In addition, liners to be worn inside of other clothing include special abbreviated panty liner taught in U.S. Pat. No. 5,729,835 by inventor Williams. This panty liner is specially designed for coupling with so-called 'thong' type underwear.

Another important liner to be worn in conjunction with outer garments includes the devices and articles taught by Lampman in U.S. Pat. No. 4,905,323. These devices serve the need for cleanliness while trying on clothing in consideration of purchase. Use of these devices permits one to fit new clothing without exposing the clothing to undesirable contact.

A comfortable pair of underwear is presented as the invention of U.S. Pat. No. 6,247,184. These articles are simple liners to be used in conjunction with outer garments such as pants. They may be fashioned as disposable and therefore might be considered relevant to principle concepts of the present disclosure.

Finally, a disposable pant liner is presented and taught by Johnson of Burbank, Calif. in recent U.S. Pat. No. 6,406,462.

In contrast to the prior art, the present invention provides a panty substitute that is configured to provide an underwear function and feel without bunching or forming visible lines in the pants when worn by the person.

SUMMARY OF THE INVENTION

The present invention is directed to an article of clothing that is a panty substitute suited for being applied to the interior surface of the crotch area of the outer garment, which outer garment is a pair of pants, including methods of use of those articles. It is a primary function of these a primary function of these articles and methods to provide an underwear or panty function without causing visible panty lines in the person's outer garment. In a preferred embodiment, the panty substitute consists of a layer of woven cloth, less than 2 millimeters in thickness, and an adhesive for affixing the layer of cloth to an interior surface of a crotch area of a pair of pants on one side of the cloth. The adhesive being suitable for bonding the substrate to an interior surface of the crotch area of an interior surface of a pair of pants. The panty substitute is designed and is shaped to fit and conform to the crotch area of the pants to provide an underwear function without bunching or forming visible lines in the pants. Preferably the panty substitute has a nonreinforced peripheral edge and a thickness of less than 2 millimeters and/or an area not greater than 150 square centimeters. The adhesive is preferably suitable for bonding the cloth to the interior surface of the crotch area of the pants so that the panty substitute is affixed firmly to the crotch area of the pants and remains in place while being worn by a person. In one preferred embodiment, the panty substitute is shaped to fit and conform to the crotch area of the pants in a geometry of a saddle and in another the panty substitute further consists of a removable protective material applied to the adhesive to prevent inadvertent contact of the adhesive with foreign matter prior to use.

A substrate of cloth material forms a special layer which is applied to an interior surface of an outer garment such as tight fitting pants. Properly applied, the article forms to the complex curved shape of the pants interior while providing an undergarment function, i.e., affording a protective layer between a person and her clothing. The article prevents the pants from being soiled allowing them to stay fresh and clean while also providing chaffing protection to sensitive flesh.

A flexible cloth material is arranged in a special shape and fashion to cooperate with the interior of pants while being worn. The shape these pant liners will adapt to is approximated by the geometry of a saddle, i.e., the shape formed at the inseam junction of a pair of trousers at the crotch area. In a first direction, the curve is downwardly concave, while in an orthogonal direction the curve is upwardly concave.

In addition, these pant liner articles have two sides. A first side has adhesive applied thereto which holds and couples the article to the pants interior when properly applied. A second side is a soft absorbent material appropriate for contact with flesh. The second side provides comfort and cleanliness functionality.

After use, the article may be easily removed from the pants for disposal. The pants may thereafter be laundered normally. In some versions, a more durable article may be prepared for laundering and re-use.

The present invention allows one to go 'underwear less' while still affording the function, benefits and protections typically provided by underwear. Preferably, the panty substitute has a butterfly shaped periphery and/or has relief cuts to further prevent wrinkling when worn. Advantageously, in one embodiment the cloth preferably is a cotton, cotton blend, silk, or silk blend and typically has an area not greater than 150 square centimeters.

The present invention is thin and suitable for coupling to the crotch area of an outer garment such as pants. Preferably the panty substitute has graphics and/or scents on the cloth and has a nonreinforced peripheral edge. In one preferred embodiment of the invention, the panty substitute consists of a layer of cloth, an adhesive on one side of the cloth, and a removable protective material applied to the adhesive to prevent inadvertent contact of the adhesive with foreign matter prior to use, the cloth shaped to fit and conform to an interior surface of a crotch area of a pair of pants to provide an underwear function without bunching or forming visible lines in the pants, the panty substitute having a nonreinforced peripheral edge, a thickness of less than 2 millimeters, and an area not greater than 150 square centimeters, the adhesive being suitable for bonding the panty substitute to the interior surface of the crotch area of the pair of pants so that the panty substitute is affixed firmly to the pants and remains in place while being worn. The present invention is further directed to method of providing an underwear function to a person wearing a pair of pants without panties and without forming visible lines in the pants. The method comprises applying a panty substitute described herein to an interior surface of a crotch area of a pair of pants and wearing the pants with the panty substitute attached to the crotch area of the pants to provide an underwear function without any visible panty lines in the pants.

OBJECTIVES OF THE INVENTION

It is a primary object of these inventions to provide the protections of underwear.

It is an object of these inventions to provide protections of underwear without discomfort associated therewith.

It is a further object to provide protection of underwear without unsightly panty lines.

A better understanding can be had with reference to detailed description of preferred embodiments and with reference to appended drawings. Embodiments presented are particular ways to realize the invention and are not inclusive of all ways possible. Therefore, there may exist embodiments that do not deviate from the spirit and scope of this disclosure as set forth by the claims, but do not appear here as specific examples. It will be appreciated that a great plurality of alternative versions are possible.

BRIEF DESCRIPTION OF THE DRAWING FIGURES

These and other features, aspects, and advantages of the present invention will become better understood with regard to the following description, appended claims and drawings where:

PREFERRED EMBODIMENTS OF THE INVENTION

Figure 1:
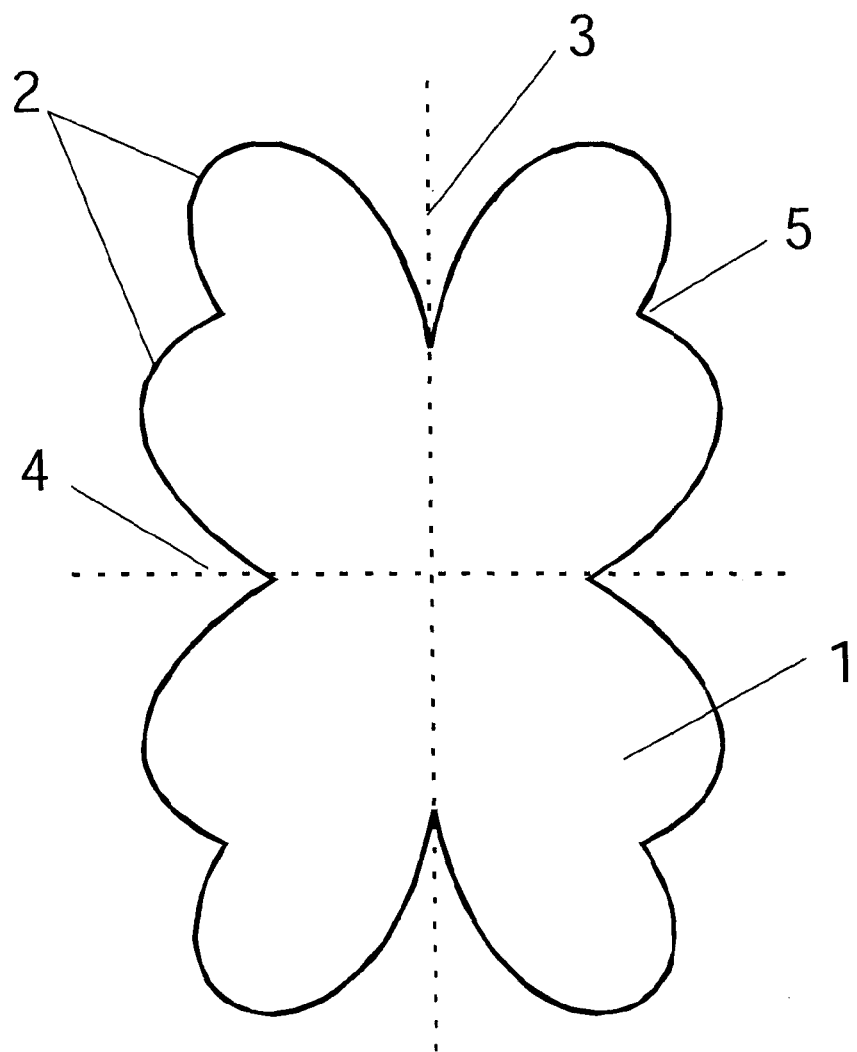
FIG. 1 illustrates a version of this invention.

In accordance with each of preferred embodiments of the present invention, garment liner, i.e., a panty substitute, and methods of use of same are provided. It will be appreciated that each of the embodiments described include an article and method and that the article and method of one preferred embodiment may be different than the article and method of another embodiment.

A thin multi-layer sheet is configured to be applied to and to cooperate with the crotch area of an outer garment. More particularly, in preferred modes of use, these articles may be applied to the interior surface of a pair of pants at the inseams junction, the crotch area of the pants. Such application is temporary and removable. In place, the article affords protection of the pants and further protection of the user. Pants are protected against soiling while the wearer is protected from the coarse materials from which pants are made. The article provides underwear like protection to the outer garment. Clothing such as jeans type pants made of denim tends to be rough and coarse and not appropriate for contact with delicate flesh. Thus, when these articles are properly applied and worn, they tend to protect the wearer from chaffing and abrasion which might occur while wearing pants without underwear. These articles serve similar function as underwear, however, clear differences provide great benefit to the user/wearer who is left without bunching or forming visible lines in the outer garment and with the feeling of being underwear less.

Saddle Shape-Fit

Preferred versions of articles of these inventions support a special fit. As they are preferably applied to interior surfaces of pants, they must accommodate the shapes taken by pants while worn. One will appreciate the flexible nature of pants and that they stretch and flex to conform to many shapes and positions. In agreement, these articles are also highly flexible and have a high stretch coefficient in two orthogonal directions. When applied to the interior surface of pants, these articles will bend, flex and stretch into any shape supported by the pants without resulting in separation therefrom. While in use, these articles remain fastened and affixed to the interior surface of the pants. In preferred versions, the article is small in size. The total area may be less than 150 square centimeters.

To support the unique shape of a pair of pants at the crotch, i.e. a saddle shape, an article may be cut from a planar substrate of cloth having a special periphery. It is not always easy to form material into complex curved shapes. Generally, when clothing is formed into the complex curves to complement the human body shape, it requires that seams be formed into a plurality of cloth segments. In consideration of the present use, these articles are preferably made without seams.

However, they must support being stretched into complex shapes. Therefore, material of a highly stretchable nature is preferred over materials which are unyielding in that regard. Materials which tend to form creases and cause 'bunching' are ruled out as candidates from which these articles should be made.

In some versions, special materials are stretchable and flexible in prescribed directions to accommodate the desired shape. Thus a sheet of cloth material to be used in forming these articles may be comprised of material having a certain directional bias to support stretching demands of the saddle shape. A sheet of material used to form these articles may actually be formed of a combination of different materials spatially distributed in accordance with a prescribed scheme to support allowing the article to adopt the saddle shape while still performing its design function.

Some preferred versions include articles formed in a manufacturing process, for example by way of molding, into a prescribed shape. A saddle shape can be impressed into a cloth material and after manufacture, the cloth material could have the tendency to hold the saddle shape thereby facilitating application to the interior surface of a pair of pants.

Periphery

Further address of the problem relating to the complex curve shape includes forming these articles from a planar substrate of cloth material with a special peripheral shape. Careful selection of a peripheral shape in view of the final shape of the device, and in further view of the coupling with the interior surface of pants, allows it to bend into a complex shape while relieving stress at the highest tension points and remain affixed to the pants. Practitioners of mathematics will point out that maximal stress lies in specific regions while others are generally relaxed. Accordingly, materials or combinations of materials more suitable for stretching can be arranged to correspond spatially to those areas of highest stretch stress.

Because these articles may be exceptionally thin at the periphery, there are no resulting panty lines. Articles formed of cloth and arranged to be durable in washing processes frequently have thick peripheral edges to prevent fraying of the material from which they are made. As preferred embodiments of these articles are disposable, their peripheral edges need not be reinforced and they may be quite thin. In this way, panty lines are completely avoided.

Material

As mentioned, these articles may preferably be formed from a cloth or cloth like material. Natural fibers such as cotton and silk are leading candidates as they are highly functional, inexpensive and suitable for contact with human skin. Blended material may also be used to provide certain benefit. Spandex materials offer great stretch quality and might be preferred in some embodiments where the articles are required to conform to surfaces characterized by extreme curves.

Portions of these articles may include materials that are preferably absorbent whereby moisture is readily received and held by the materials. In some versions, it is desirable to have an absorption layer next to a liquid barrier layer. Liquid can be absorbed into the first layer and held there without being permitted to pass the barrier layer. In these versions, the barrier layer may be disposed between the absorption layer and the pants to further provide anti-soiling protection to the pants. Thus, articles of multi-layers of various materials having different functions are fully contemplated.

Some objectives of these inventions are best served when using materials of very inexpensive nature. Preferred uses of these articles demand that they be disposable. As such, they must be formed of inexpensive materials suitable for disposal after single use. Thus, cottons and cotton blends are particularly useful for forming these articles.

As it is a primary objective to provide underwear protection without forming visible panty lines in the outer garment, the materials used to form these articles are preferably quite thin. In best modes, the materials should be about 2 millimeters or less. In this way, the article maintains its function without being so thick as to cause the outer garment to reveal its shape at the peripheries.

Special Adhesives

As the article formed of materials described above is to be coupled with the interior surface of clothing, a mechanism is required to bond the article such that it is affixed firmly and remains in place while being worn. To provide this function, an adhesive may be most suitable. While a delicate hook-and-loop mechanism, among others, is recognized as possible, these fasteners might frustrate the purpose of forming the most brief of undergarments. Therefore, best versions anticipate use of adhesives to hold the articles to the interior surface of pants.

Suitable adhesives are the type which cooperate well with materials from which the outer garment is made, i.e., cotton, wool, silk, etc. These adhesives should support the coupling in a manner which is temporary. The article is to be affixed to the pants such that it may be easily removed therefrom when desired. It is not intended that this article be permanently affixed to the pant inseams.

Not only is the coupling meant to be temporary, it is preferred that when the coupling is broken, i.e., the panty substitute is removed from the pants, the adhesive tends to stick more strongly to the panty substitute rather than to the pants. When the article is lifted away from the pants, most of the adhesive tends to stick to the article and little remains with the pants. The adhesive remaining on the pants is preferably water soluble, such that in normal laundering processes, it is removed from the pants.

Thus, adhesives are preferably arranged to have a greater adhesion with regard to the material of the article than with the pants. The adhesive is therefore disposed of together with the article after use. Adhesives appropriate for use with these articles are therefore necessarily those suitable for common disposal in public facilities.

Adhesives may be applied in the manufacturing process. After an appropriate cloth material sheet is formed with its requisite shape and size, it may be subject to the application of adhesive material to one side. As such, the article is ready for use.

In some cases, the adhesive is preferably applied immediately before the article is applied to pants. In this regard, one might use a spray adhesive whereby a user simply applies the adhesive to the prescribed side of the article just before applying the article to the correct place in the pants. Accordingly, some versions of these inventions include an article arranged to receive adhesives applied by a user just before use.

After use, the article may be easily removed from the pants for disposal. The pants may thereafter be laundered normally.

Crack-and-Peel Layer

Figure 4:
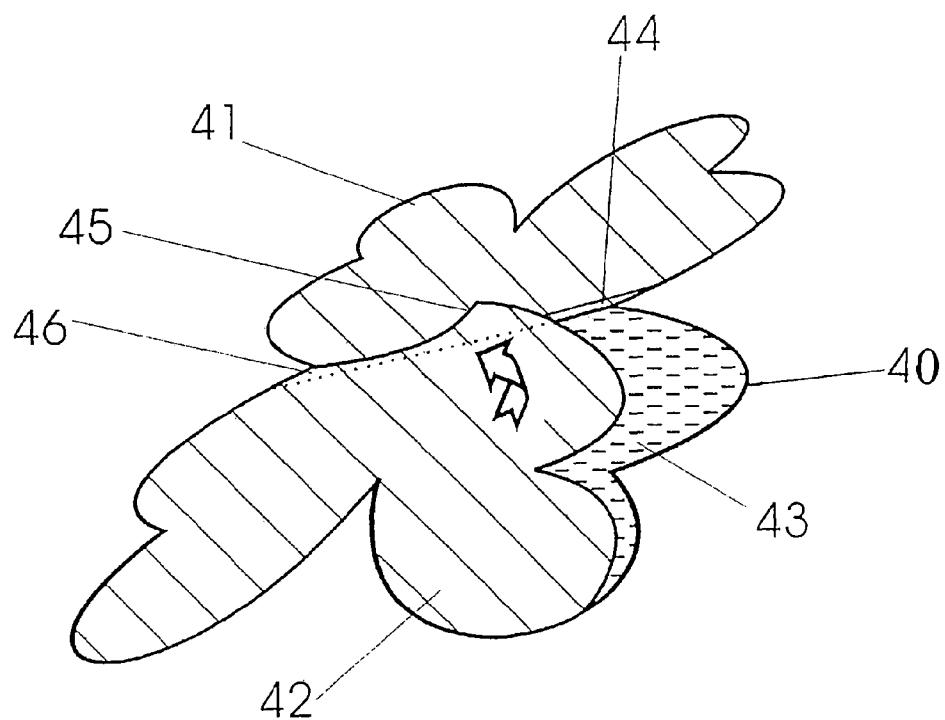
FIG. 4 is a perspective drawing to illustrate articles and their backing elements.
Figure 5:
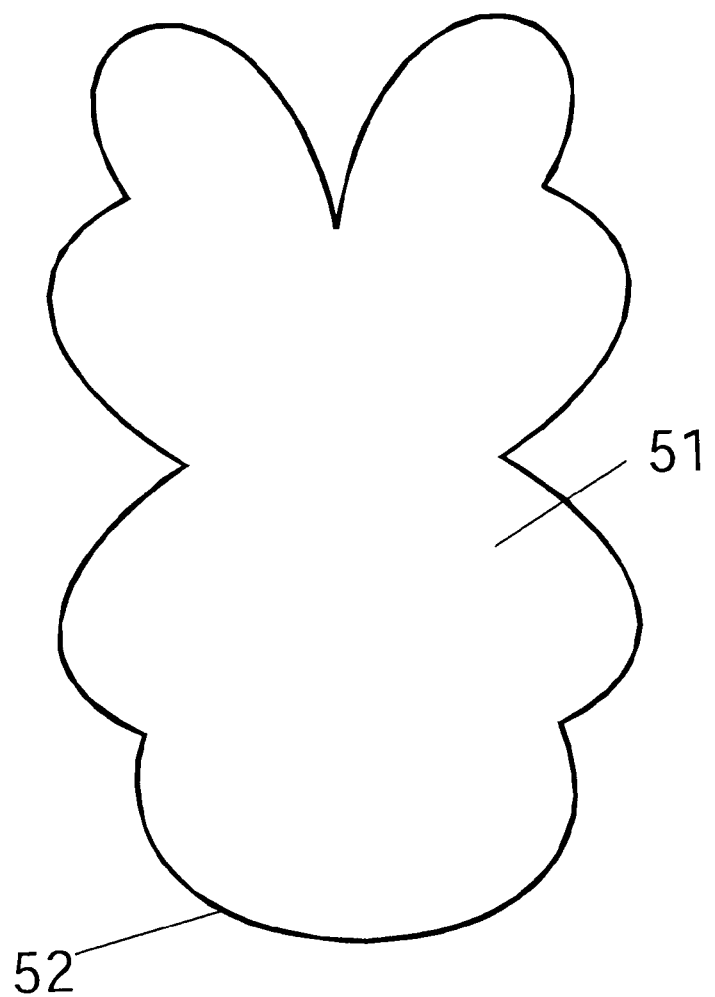
FIG. 5 illustrates a version having an alternative periphery.
Figure 6:
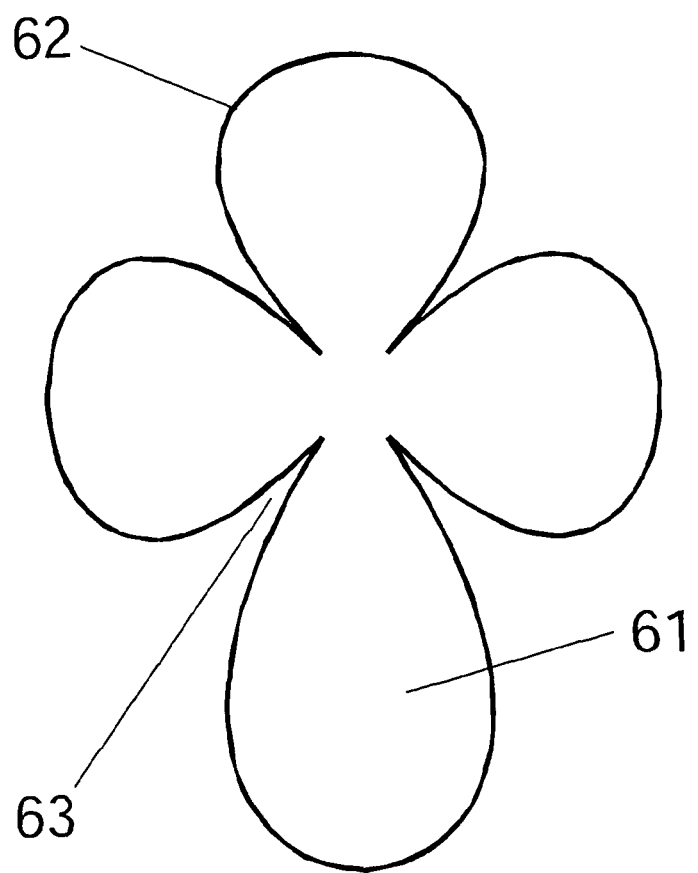
FIG. 6 is a drawing illustrating one version of a preferred periphery.

As set forth in FIG. 4, a protective layer 46 may also be used to prevent exposure of the adhesive 43 before it is to be applied to the outer garment. After adhesives 43 are applied to the cloth sheet 40, a waxed paper protective layer 46 in the same shape as the cloth can be set to the adhesive to protect it from accidental contact with foreign matter. The waxed paper protective sheet or cover 46 can be peeled away just prior to application of the article. Thus, in this embodiment, the panty substitute would consist of, a layer of cloth 40 having a thickness of less than 2 millimeters; an adhesive 43 on one side; and a removable protective material 46 applied to the adhesive. A 'crack-and-peel' arrangement of the protective cover facilitates use and is operable with articles of the present invention. Alternatively, an overlap arrangement 45 of two sheets 42 and 44 provides an 'easy-to-grab' methodology to support easy removal of the protective layer 46 at the time the article is to be applied to pants. This type of backing layer is commonly used on bandage strips and its use there is common.

In a special case, the protective layer may simply be another identical article in a stack of articles. Accordingly, a first article can be applied on top of another and still another to form a stack of a plurality of articles. When one article is removed from the stack, its adhesive is exposed and it may be applied to the interior pants surface normally. The other article members remain in the stack, each with their adhesive side being protected by another sheet. Similar to a notepad, one sheet is removed at a time for immediate use. This scheme also protects adhesives which may be applied in the manufacture process thereby relieving the user of having to apply adhesives.

Kits

These inventions include kits of a plurality of components which cooperate together.

In a first example, a kit may include several articles each cut and prepared in accordance with the description above where adhesives have not been applied to the cloth sheets. The kit also includes a container of adhesive and adhesive applicator. For example, a spray adhesive in a pressurized can or a roll-on adhesive in a ball applicator apparatus. The portion of adhesive provided in the kit is set to correspond to the number of sheets supplied in the same kit resulting in a unit of cooperating parts.

As appropriate for undergarments, certain prints and print themes might be applied in the manufacturing process to impart an attractive and pleasing look. Thus, an alternative kit of these inventions includes a plurality of pant liners having a color scheme or theme. A plurality of articles are packaged together as a single unit where each of the articles cooperates with the others in the kit by way of a matching color, color set, or theme. For example, a group of pastels or a group of 10 articles each having a different shade of pink for a package with an attractive color look.

Another kit includes a stacked pad of articles like a notepad of multiple sheets. Packaged and sold as a single unit, these kits of multiple articles are attractive in a retail sense. In addition, the articles cooperate with one another as described where a first pad protects the adhesive of an adjacent article from inadvertent contact with foreign objects.

Still further, a kit may be arranged to include a special travel pack or handy packaging. It is not so easy to travel light with a fresh change of conventional underwear. To carry extra clothes requires one to pack a clothes suitcase which is not practical on short day trips. It is difficult to accommodate soiled underwear without carrying a full luggage set with special apparatus designed for such matters. However, disposable underwear, particularly the brief type taught here, allow one to have clean fresh underwear while on travel. A ready supply may be carried in a small discrete package easily carried in the smallest of briefcases and handbags. Thus, kits of these inventions are arranged in connection with small carrying cases for travel purposes.

Fragrances and Deodorizers

Articles of these inventions have special cooperation with regard to scents. While one could dress one's underwear with regard to scent by applying an eau de toilette, generally underwear simply smells of the detergent in which it was most recently laundered. As articles of the instant inventions are disposable, they support being decorated with pleasing scents. A package of these garment liner articles can be prepared with perfumes and fragrances to impart a pleasant smell thereto. In addition, it is possible to use a deodorizing chemistry in conjunction with the articles where that result is desirable. Unlike common reusable underwear which does not support being used Themes Users of common underwear have enjoyed combining art of a graphical nature with their intimate wear. Indeed, nearly anyone could attest to having at least seen a pair of Santa Claus boxers. It is an important part of good undergarments that they include support for carrying a graphical theme or other art of printed form. Thus, articles of the present invention fully anticipate combination with artistic themes by way of printed matter thereon. In some cases, mere coloring constitutes application of art to these articles. A pleasing pastels group of colors may be appropriately applied to preferred articles as those colors are associated with softness and tend to further associate the articles with comfort. A kit of these inventions may include a plurality of articles each having a different print from the other, however that print being related to the others such that the articles all clearly belong to a group.

In the interests of completeness, a general description of devices and the elements of which they are comprised as well as methods and the steps of which they are comprised is presented here following with reference to the appended drawing figures.

FIG. 1 illustrates a substrate 1 of these inventions. The material may be cut from a cloth stock at a specially designed butterfly-shaped periphery 2. The axes 3 and 4 each correspond to a forward-back and left-right inseam found in a common pair of trousers or pants. The periphery may be formed with a view to decreasing wrinkling when a flat sheet is bent into a complex curved shape. The periphery supports relief points 5 strategically placed in certain pressure positions.

Figure 2:
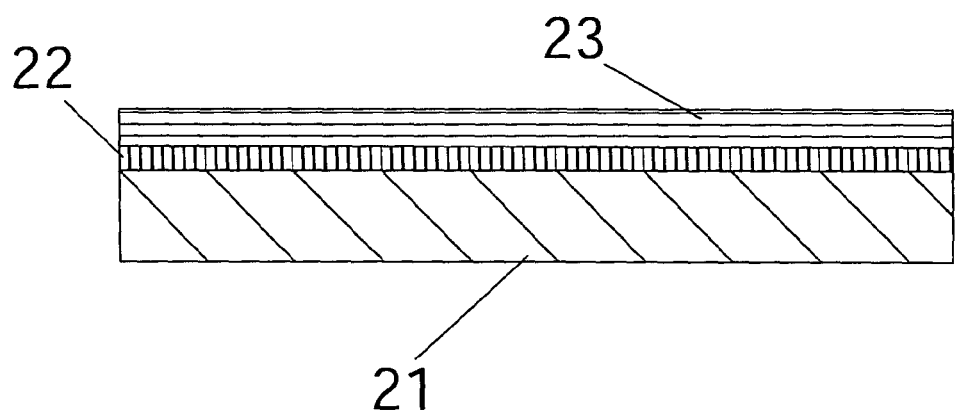
FIG. 2 is a cross section view to illustrate important layers of these articles.

A cross-sectional view is shown in FIG. 2. One will appreciate that what is referred to as a single article herein may actually be a combination of several material layers laminated together. For example, one version may include a highly absorbent layer of cotton material 21 to which is bonded a vapor bather layer 22 and finally an adhesive layer 23. The adhesive layer, when placed into contact with the interior surface of an outer garment, holds the article in place. The vapor barrier layer prevents liquids from passing to the adhesive and further to the outer garment. The absorbent layer functions to absorb and hold liquids.

Figure 3:
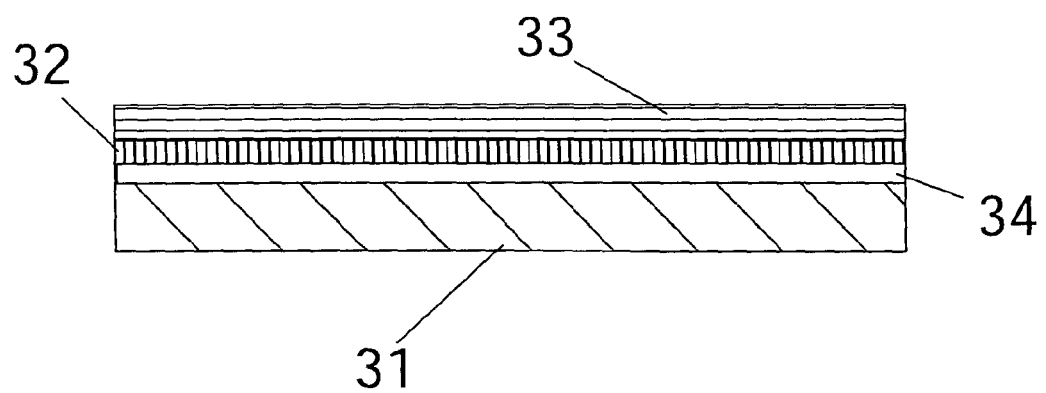
FIG. 3 is an alternative cross section.

Another version, as shown in FIG. 3, may have four layers as follows. An absorption layer 31, next to a bather layer 34 and adhesive layer 32 with a fourth layer being a wax paper cover sheet 33 added to protect the adhesive against inadvertent contact prior to use. In this way, that article may be carried about in a purse before it is to be used without contamination to the adhesive surface. Where an article of such type is used, the paper protective layer in two parts 46 having overlapping arrangement 45 may be easily removed before use. FIG. 4 illustrates this function. A user may hold the article at point 41 and pull a first half 42 of the paper cover away from the adhesive surface 43 to which it was bonded. Thereafter, the other half 44 of the paper cover may be pulled away.

It is not necessary that the periphery be symmetrical. Other shapes are fully anticipated. Where it is desirable to have greater protection distributed about various areas, an article 51 may preferably have a periphery 52. Other shapes similarly support other functions. Article 61 may be used with materials which do not stretch so easily. Special periphery 62 is designed with relief cuts 63. The highest tension regions are relieved by these relief cuts when the article is applied to pants and takes a complex curved shape.

Figure 7:
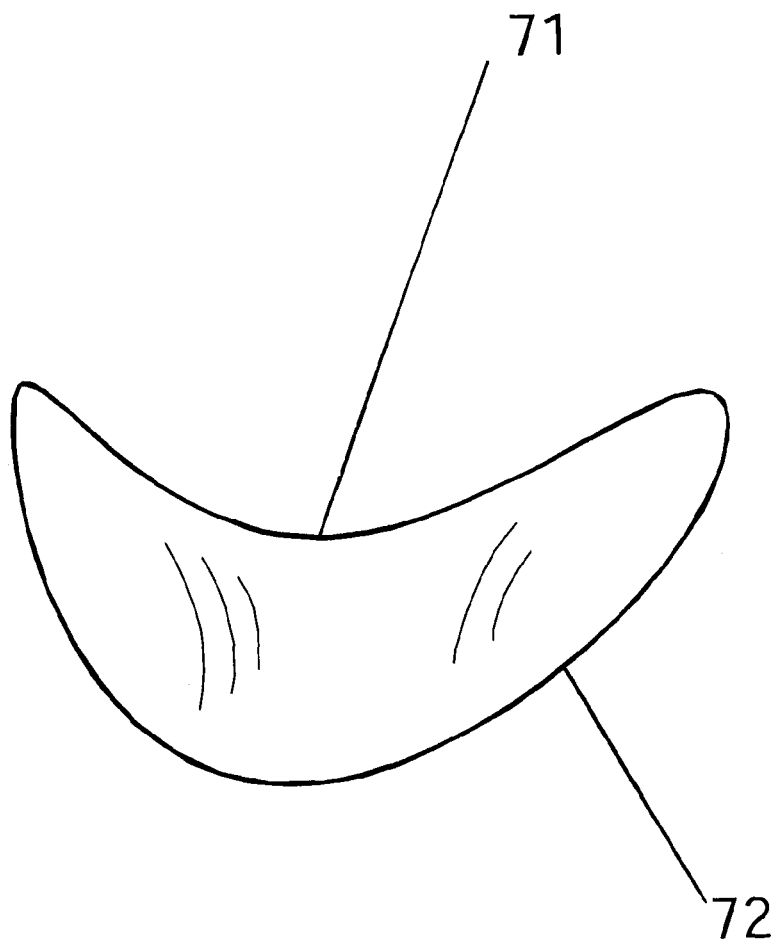
FIG. 7 shows a drawing of a preformed version.
Figure 8:
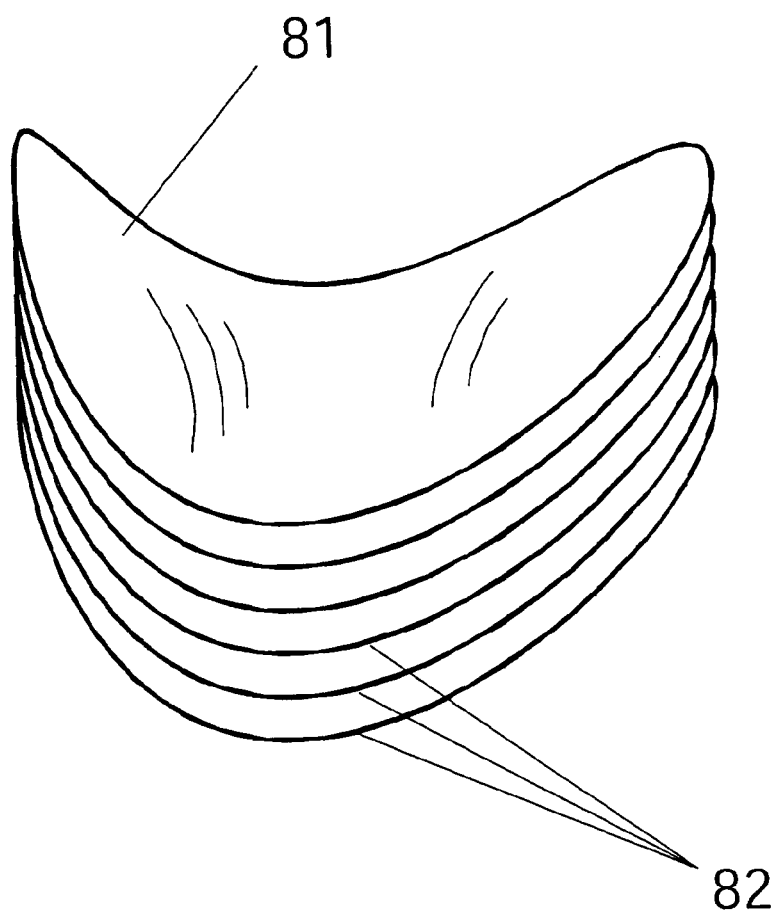
FIG. 8 shows a kit having a plurality of similar articles in a group.
Figure 9:
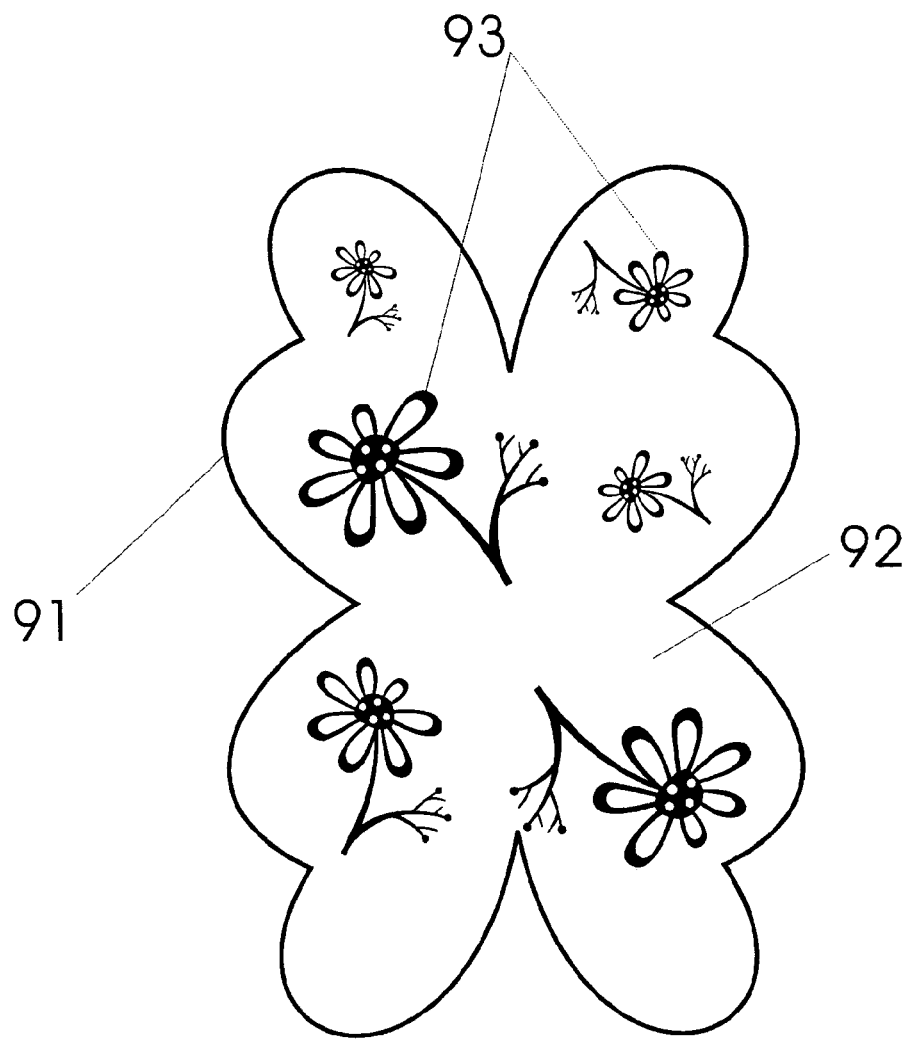
FIG. 9 illustrates graphical indicia printed on a top surface.

While the shapes mentioned are quite useful, there are other shapes which will serve the purpose and essence of this invention as well. Where the manufacturing processes include formation of shaped articles of three dimensions, the shape shown in FIG. 7 may be useful. The preformed shape includes a concave up region 71 (left to right on the page) and an underside which is concave down. In this case, the periphery 72 may not have a complex shape but rather smooth and continuous.

One nice feature supported by the preformed versions is that a stack of a plurality of the articles may be prepared as a collection of articles. A first article 81 in the shape of a saddle may have a plurality of many other articles 82 thereunder.

Methods

The present invention is meant to include methods. Specifically, methods of going without underwear. More precisely, methods of preparing the outer garment prior to wearing. The steps of these methods may be taken for the purpose of providing an underwear function without actual use of underwear. These methods include application of the underwear substitute described above to the interior surface of the outer garment.

The methods may best be characterized as follows:

Methods of preparing the outer garment prior to wearing for the purpose of protecting one's outer garments without the use of underwear include the step of applying a protective panty substitute to the interior surface of the outer garment.

These methods are more completely defined where said 'applying' includes pressing an article prepared with an adhesive to the crotch area of the interior surface of an outer garment. The methods are preferably with respect to 'outer garments' described as either of the following: pants, shorts, pant-skirts, pantsuits, DANSKINS bodywear, bodyhose, or similar. After application of article, one simply wears the outer garment normally without further modification or attention.

Methods of this invention further include additional steps taken after wearing. For example, a method may include the steps necessary to return the clothing to its normal state after use. Thus, a step of these methods may include removal of the article from the clothing. This may be accomplished by grasping one edge of the article and pulling away from the outer garment. In addition, methods include the step of disposal. These articles are suitably designed to be properly disposed of in common trash receptacles. Thus, after use, they may be simply thrown away.

Additionally, some methods include the step of washing the outer garment. In some instances, the outer garment may be left with slight adhesive residue. Therefore, a complete description of use of these articles includes a step taken to assure the outer garment is returned to its proper state. Normal washing in common laundry processes is sufficient to remove any leftover adhesives from the outer garment. Accordingly, some of these methods include the step of washing the outer garment.

In some versions, a step before applying the article includes one in which an adhesive is applied to one side of the article. In the case where adhesives are not applied in the manufacturing process, an added step requires a user to apply adhesives. Preferably, a user might use a spray adhesive which can be easily applied to the appropriate side of an article suitably arranged for such. In this case, spray adhesive is applied, thereafter, the article is pushed onto the interior surface of the outer garment at the inseams junction, and the clothing is worn normally.

In some versions, a step before applying the article includes one in which a protective layer is removed from an adhesive. In the case where a 'crack-and-peel' wax paper coating, or similar coating, protects the article prior to use, the wax paper coating must be removed from the article before it can be applied to the pants. Thus, methods of these versions of the invention include removal of the wax paper coating prior to the step applying the article to the inside of the outer garment.

One will now fully appreciate how disposable liners applied to the outer garment serve an underwear function. Although the present invention has been described in considerable detail with clear and concise language and with reference to certain preferred versions thereof including the best mode anticipated by the inventor, other versions are possible. Therefore, the spirit and scope of the invention should not be limited by the description of the preferred versions contained therein, but rather by the claims appended hereto.

What is claimed is:

1. A method of providing an underwear function to a person wearing an outer garment without panties, which outer garment is a pair of pants, the method comprising applying a panty substitute to an interior surface of a crotch area of the pants and wearing the pants with the panty substitute attached to the crotch area, wherein the panty substitute consists of a layer of material and an adhesive on one side of the material for affixing the panty substitute to the interior surface of the crotch area of the pants, the material configured to fit and conform to the crotch area of the pants in a geometry of a saddle to provide an underwear function without bunching or forming visible lines in the pants, the panty substitute having a thickness of less than 2 millimeters and the adhesive being suitable for bonding the material to the interior surface of the crotch area of the pants so that the panty substitute is affixed firmly to the pants and remains in place to provide an underwear function without bunching or forming visible lines in the pants when worn.

2. The method of claim 1, wherein the panty substitute has an area not greater than 150 square centimeters and the layer of material is a cloth.

3. The method of claim 1, wherein the layer of material is woven and comprises a cotton material or a silk material.

4. The method of claim 1, wherein the layer of material has relief cuts to prevent wrinkling of the panty substitute when worn.

5. A panty substitute having an area not greater than 150 square centimeters and a thickness of less than 2 millimeters and consisting of a layer of material, wherein the material comprises spandex; an adhesive on one side, the adhesive suitable for bonding the material to an interior surface of an outer garment; and a removable protective material applied to the adhesive to prevent inadvertent contact of the adhesive with foreign matter prior to use, wherein the panty substitute is configured to provide an underwear function without bunching or forming visible lines in the outer garment when worn by the person.

6. The panty substitute of claim 5, wherein the removable protective material is a wax paper.

7. The panty substitute of claim 6, wherein the removable protective material is formed in two portions with a crack and peel mechanism joining those two portions.

8. The panty substitute 5, wherein the removable protective material is formed in two portions with an overlap arrangement to facilitate an easy grasp function.

9. The panty substitute of claim 5, having a butterfly shaped periphery.

10. The panty substitute of claim 5, wherein the layer of material is cloth.

11. The panty substitute of claim 5, wherein the layer of material has relief cuts to prevent wrinkling of the panty substitute when worn.

12. The panty substitute of claim 5, wherein the layer of material is shaped to fit and conform to the crotch area of the pants in a geometry of a saddle to provide an underwear function and feel.

\* \* \* \* \*